US 7,067,061 B2

(12) United States Patent
Bosetto et al.

(10) Patent No.: US 7,067,061 B2
(45) Date of Patent: Jun. 27, 2006

(54) METHOD AND A DEVICE FOR PREPARING A MEDICAL LIQUID

(75) Inventors: Antonio Bosetto, Mirandola (IT);
Francesco Paolini, Modena (IT)

(73) Assignee: Gambro Hospal (Schweiz) AG, Basel (CH)

( * ) Notice: Subject to any disclaimer, the term of this patent is extended or adjusted under 35 U.S.C. 154(b) by 0 days.

(21) Appl. No.: 10/844,422

(22) Filed: May 13, 2004

(65) Prior Publication Data

US 2004/0206703 A1 Oct. 21, 2004

Related U.S. Application Data

(63) Continuation of application No. 09/869,712, filed as application No. PCT/IB00/01588 on Nov. 2, 2000, now Pat. No. 6,793,827.

(30) Foreign Application Priority Data

Nov. 2, 1999 (IT) .............................. TO99A0948

(51) Int. Cl.
*B01D 61/26* (2006.01)
*B01D 35/00* (2006.01)
*A61M 37/00* (2006.01)
*B01D 61/28* (2006.01)
*B01D 61/32* (2006.01)

(52) U.S. Cl. ...................... 210/647; 210/645; 210/646; 210/739; 210/746; 210/321.71; 210/143; 210/929; 210/85; 210/86; 210/97; 210/101; 210/134; 604/5.01; 604/6.11; 604/65; 604/67

(58) Field of Classification Search .................. 210/85, 210/86, 97, 101, 134, 142, 143, 929, 321.71, 210/646, 647, 739, 746; 604/4.01, 5.01, 604/28, 30, 31, 48, 500, 506, 6.11, 65, 67
See application file for complete search history.

(56) References Cited

U.S. PATENT DOCUMENTS 4,136,708 A 1/1979 Consentino et al.

(Continued)

FOREIGN PATENT DOCUMENTS

FR 2 504 817 11/1982
WO WO 95/08299 3/1995

*Primary Examiner*—John Kim
*Assistant Examiner*—Krishnan S. Menon
(74) *Attorney, Agent, or Firm*—Finnegan, Henderson, Farabow, Garrett & Dunner, L.L.P.

(57) ABSTRACT

A method for preparing a medical liquid from a liquid, such as water, and two concentrated solutions comprises the following steps:
  circulating the liquid in a conduit (15), at a flowrate Q0;
  injecting into the conduit (15), at a flowrate Q1, a first concentrated solution containing a first ionic substance A and a second ionic substance B, the ionic substances A and B having, respectively, in the first concentrated solution, a concentration [Asol] and a first concentration [B1sol];
  injecting into the conduit (15), at a flowrate Q2, a second concentrated solution containing the first ionic substance A and the second ionic substance B, the first ionic substance A having, in the second concentrated solution, the same concentration [Asol] as in the first concentrated solution, and the second ionic substance B having, in the second concentrated solution, a second concentration [B2sol] different than the first concentration [B1sol] in the first concentrated solution;
  regulating the injection flowrate Q1 and the injection flowrate Q2 of the first and second concentrated solutions in such a way that at any given time the diluted solution resulting from the mixing of the liquid and the concentrated solutions has a desired concentration [Ades] of first substance A and a desired concentration [Bdes] of second substance B.

8 Claims, 3 Drawing Sheets

U.S. PATENT DOCUMENTS

| | | |
|---|---|---|
| 4,923,613 A | 5/1990 | Chevallet |
| 5,091,094 A | 2/1992 | Veech |
| 5,244,568 A | 9/1993 | Lindsay et al. |
| 5,346,472 A | 9/1994 | Keshaviah et al. |
| 5,567,320 A | 10/1996 | Goux et al. |
| 5,578,223 A | 11/1996 | Bene et al. |
| 5,616,248 A | 4/1997 | Schal |
| 6,635,026 B1 | 10/2003 | Bene |

METHOD AND A DEVICE FOR PREPARING A MEDICAL LIQUID

This is a continuation of application Ser. No. 09/869,712, filed Oct. 9, 2001 now U.S. Pat. No. 6,793,827, which is incorporated herein by reference which is a 371 of PCT Application No. PCT/IB00/01588 filed Nov. 2, 2000.

The present invention relates to a method and a device for preparing a medical liquid.

The invention has an application in particular in the treatment of renal insufficiency, where it can be used for preparing a dialysis liquid. In this context, the invention is particularly suitable for treating patients whose internal medium presents an excess of potassium.

The kidneys perform many functions, including elimination of water, excretion of catabolites (or waste products of metabolism, such as urea and creatinine), regulation of the concentration of electrolytes in the blood (sodium, potassium, magnesium, calcium, bicarbonates, phosphates, chlorides), and regulation of the acid-base balance of the internal medium, which balance is obtained in particular through the elimination of weak acids (phosphates, monosodium acids) and through the production of ammonium salts.

In persons who have lost the use of their kidneys, since these excretory and regulatory mechanisms no longer function, the internal medium becomes charged with water and waste products of metabolism and presents an excess of electrolytes (sodium in particular), and, in general, acidosis, with the pH of the blood plasma shifting towards 7.

To remedy kidney dysfunction, the conventional practice is to treat the blood by extracorporeal circulation in a semipermeable membrane exchanger (hemodialyzer), with circulation, on either side of the membrane, of the patient's blood and of a dialysis liquid comprising the main electrolytes of the blood (chlorides, bicarbonates, sodium, calcium, potassium, magnesium) in concentrations close to those of the blood of a healthy subject. As a result of the physical phenomenon called dialysis, the molecules migrate from the liquid in which their concentration is highest to the liquid in which their concentration is lowest.

A significant electrolytic change in uremic patients is the increase in the potassium concentration of the plasma. Now, hyperkalemia (too high a concentration of potassium) is associated with incidents linked to hyperpolarization of the membrane of the neuromuscular cells, which can result in hypokinetic arrhythmia and complete atrioventricular block. One of the objectives of dialysis treatment is therefore to eliminate the excess potassium accumulated by the patients between two treatment sessions. In accordance with the physical principle cited above, the quantity of potassium eliminated during treatment depends directly on the difference between the concentration of the potassium in the plasma and the concentration of the potassium in the dialysis liquid, which is generally fixed at a constant level, less (approximately 2 mEq/l) than the physiological level (approximately 3.5 mEq/l).

At the start of conventional dialysis treatment, a patient with hyperkalemia (whose plasma potassium concentration can be as high as 10 mEq/l) is exposed to the undesirable effects resulting from the considerable difference between the potassium concentration of his plasma and that of the dialysis liquid: this increased gradient in fact causes a substantial diffusive flow of potassium across the membrane of the hemodialyzer, which in turn causes a substantial flow of potassium across the membrane of the cells, which affects the electric potential of the membrane at rest and, consequently, the cellular excitability. As this mechanism also influences the cardiac pacemaker cells, the patent runs the risk of cardiac arrhythmia during the dialysis treatment. This phenomenon is naturally heightened in cases of cardiac weakness and can lead to a reduction in the ejection volume affecting the cardiovascular circulation.

A particular object of the invention is therefore to modify the conditions of conventional dialysis treatment, without however affecting its effectiveness, in such a way that patients with hyperkalemia are no longer exposed to the risks mentioned above.

A general object of the invention is to conceive a device and a method for preparing a treatment liquid which can be used for extracorporeal treatment of blood, and by means of which the concentration of two ionic substances can be adjusted separately, in particular sodium and potassium (or calcium, or magnesium).

According to the invention, this object is achieved by means of a method for preparing a medical liquid from a liquid, such as water, and two concentrated solutions, comprising the following steps:

circulating the liquid in a conduit, at a flowrate $Q0$;

injecting into the conduit, at a flowrate $Q1$, a first concentrated solution containing a first ionic substance A and a second ionic substance B, the ionic substances A and B having, respectively, in the first concentrated solution, a concentration $[Asol]$ and a first concentration $[B1sol]$;

injecting into the conduit, at a flowrate $Q2$, a second concentrated solution containing the first ionic substance A and the second ionic substance B, the first ionic substance A having, in the second concentrated solution, the same concentration $[Asol]$ as in the first concentrated solution, and the second ionic substance B having, in the second concentrated solution, a second concentration $[B2sol]$ different than the first concentration $[B1sol]$ in the first concentrated solution;

regulating the injection flowrate $Q1$ and the injection flowrate $Q2$ of the first and second concentrated solutions in such a way that at any given time the diluted solution resulting from the mixing of the liquid and the concentrated solutions has a desired concentration $[Ades]$ of first substance A and a desired concentration $[Bdes]$ of second substance B.

According to one characteristic of the invention, the injection flowrate $Q1$ and the injection flowrate $Q2$ of the concentrated solutions A and B are varied over the course of time in such a way that the concentration of the second substance B in the diluted solution varies over the course of time in accordance with a predetermined profile.

According to another characteristic of the invention, the flowrate $Q0$ of the liquid in the conduit is constant, and the sum of the injection flowrates $Q1+Q2$ of the concentrated solutions A and B is maintained constant in such a way that the concentration of the first substance A in the diluted solution remains substantially constant.

According to yet another characteristic of the invention, the injection flowrate $Q1$ and the injection flowrate $Q2$ of the concentrated solutions A and B are varied over the course of time in such a way that the concentration of the first substance A in the diluted solution varies over the course of time in accordance with a predetermined profile.

The invention also relates to a device for preparing a treatment liquid from a liquid, such as water, and two concentrated solutions, comprising:

a conduit with a first end intended to be connected to a source of liquid, such as water, and a second end for delivering a treatment liquid;

first injection means for injecting into the conduit, at a flowrate Q1, a first concentrated solution containing a first ionic substance A and a second ionic substance B, the ionic substances A and B having, respectively, in the first concentrated solution, a concentration [Asol] and a first concentration [B1sol];

second injection means for injecting into the conduit, at a flowrate Q2, a second concentrated solution containing the first ionic substance A and the second ionic substance B, the first ionic substance A having, in the second concentrated solution, the same concentration [Asol] as in the first concentrated solution, and the second ionic substance B having, in the second concentrated solution, a second concentration [B2sol] different than the first concentration [B1sol] in the first concentrated solution;

regulating means for regulating the first and second injection means and for adjusting the injection flowrate Q1 and the injection flowrate Q2 of the first and second concentrated solutions in such a way that at any, given time the diluted solution resulting from the mixing of the liquid and the concentrated solutions has a desired concentration [Ades] of first substance A and a desired concentration [Bdes] of second substance B.

In one embodiment of the invention, the device for preparing treatment liquid is incorporated in a hemodialysis system, the substance A is sodium and the substance B is potassium, calcium, or magnesium. As the sodium concentration in a dialysis liquid is much higher than the potassium (calcium or magnesium) concentration, the potassium concentration can be very precisely regulated by measuring the conductivity of the mixture forming in the conduit immediately downstream of the site of injection of the first concentrated solution into the conduit, and of the mixture forming in the conduit immediately downstream of the site of injection of the second concentrated solution into the conduit (there is an excellent correlation between the conductivity of a solution and its sodium concentration).

Moreover, there is no danger of influencing the plasma potassium or calcium concentration of a patient using a very dilute dialysis solution prepared and administered by a system equipped with reliable means for measuring concentrations, which would not be the case if this objective were achieved by injection of more concentrated solution.

The invention also relates to a kit of solutions for extracorporeal treatment of blood, comprising two concentrated solutions and a bag with two compartments intended to contain each of the solutions from the kit. Each of the solutions contains at least two ionic substances A and B, the ionic substance A having the same concentration in the two solutions and the ionic substance B having different concentrations in two solutions.

According to one characteristic of the invention, the two solutions are identical except for one ionic substance whose concentration differs from one solution to the other.

Other characteristics and advantages of the invention will become more apparent on reading the following description. Reference will be made to the attached drawings, in which.

Figure 1:
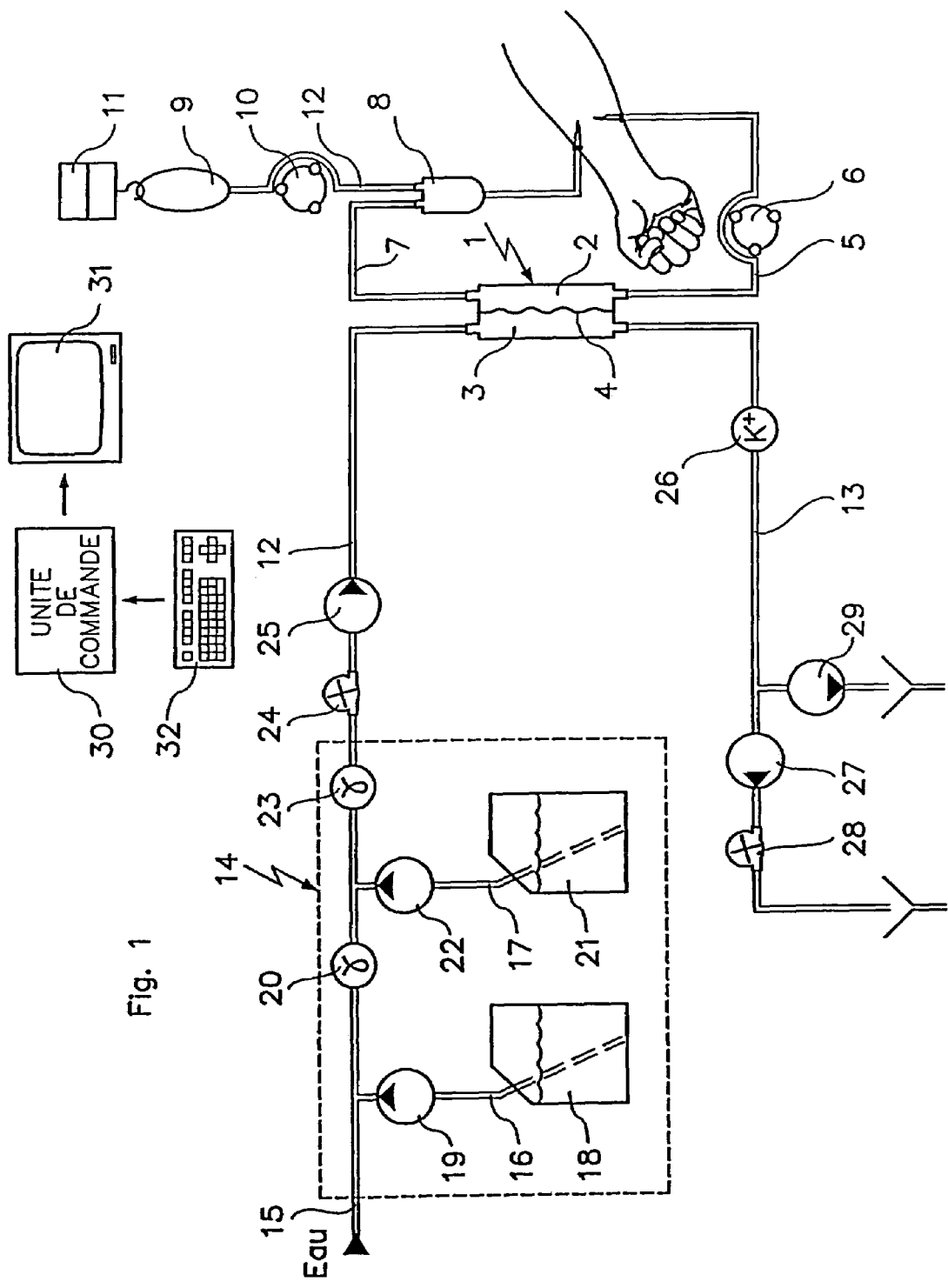
FIG. 1 is a diagram showing a device for treatment of blood.

The hemodialysis system shown in FIG. 1 comprises a hemodialyzer 1 with two compartments 2, 3 separated by a semipermeable membrane 4. A first compartment 2 has an inlet connected to a blood withdrawal conduit 5 on which a circulation pump 6 is arranged, and an outlet connected to a blood return conduit 7 on which a bubble trap 8 is interposed.

An infusion device comprising a pump 10 and a balance 11 is provided for injecting into the bubble trap 8 the contents of a bag 9 of infusion liquid containing sodium bicarbonate. The bag 9 is suspended from the balance 11 and it is connected to the bubble trap 8 via a conduit 12 on which the infusion pump 10 is arranged. The balance 11 serves to control the pump 10 so that the flowrate of the infusion liquid is equal to a reference flowrate.

The second compartment 3 of the hemodialyzer 1 has an inlet connected to a conduit 12 for supply of fresh dialysis liquid, and an outlet connected to a conduit 13 for removal of spent liquid (dialysis liquid and ultrafiltrate).

The supply conduit 12 connects the hemodialyzer 1 to a device 14 for preparing dialysis liquid, comprising a main conduit 15 whose upstream end is intended to be connected to a source of running water. First and second subsidiary channels 16, 17 are connected to this main conduit 15.

According to the invention, the free end of the first subsidiary conduit 16 is intended to be immersed in a container 18 for a first concentrated saline solution containing sodium chloride, calcium chloride, magnesium chloride and potassium chloride. This first conduit 16 is equipped with a pump 19 for metering the first concentrated solution into the dialysis liquid, which is controlled as a function of the comparison between 1) a first reference value of conductivity for the solution forming at the junction of the main conduit 15 and the first subsidiary conduit 16, and 2) the value of the conductivity of this solution measured by means of a first conductivity probe 20 arranged on the main conduit 15 immediately downstream of the junction between the main conduit 15 and the first subsidiary conduit 16.

According to the invention, the free end of the second subsidiary conduit 17 is intended to be immersed in a container 21 for a second concentrated saline solution containing sodium chloride, calcium chloride, magnesium chloride and potassium chloride. This second solution contains the same ionic substances as the first solution and in the same concentrations, except for potassium whose concentration is different. The second conduit 17 is equipped with a pump 22 for metering the second concentrated solution into the dialysis liquid, which is controlled as a function of the comparison between 1) a second reference value of conductivity for the solution forming at the junction of the main conduit 15 and the second subsidiary conduit 17, and 2) the value of the conductivity of this solution measured by means of a second conductivity probe 23 arranged on the main conduit 15 immediately downstream of the junction between the main conduit 15 and the second subsidiary conduit 17.

The conduit 12 for supply of dialysis liquid forms the continuation of the main conduit 15 of the device 14 for preparation of dialysis liquid. Arranged on this supply conduit 12, in the direction of circulation of the liquid, are a first flowmeter 24 and a first circulation pump 25.

The downstream end of the conduit 13 for removal of spent liquid is intended to be connected to the drain. Arranged on this conduit, in the direction of circulation of the liquid, are a probe 26 for measuring the potassium concentration, a second circulation pump 27, and a second flowmeter 28. An extraction pump 29 is connected to the removal conduit 13 upstream of the second circulation pump 27.

The hemodialysis system represented in FIG. 1 also comprises a calculation and control unit 30. This unit is connected to a screen 31 and to a keyboard 32 via which the user inputs various reference values: flowrate reference values (blood flowrate Qb, dialysis liquid flowrate Qd, infusion solution flowrate Qinf), reference values for concentration of ionic substances in the dialysis liquid, reference value for the duration of treatment T, reference value for loss of weight WL. Moreover, the calculation and control unit 30 receives information emitted by the measurement elements of the system, such as the flowmeters 24, 28, the conductivity probes 20, 23, and the probe 26 for measuring potassium concentration. As a function of the instructions received and of programmed operating modes and algorithms, it controls the drive elements of the system, such as the pumps 6, 10, 19, 22, 25, 27, 29.

According to the invention, the concentration of sodium and the concentration of potassium in the dialysis liquid can be adjusted independently of one another: for a constant flowrate Q0 of water, the concentration of sodium depends on the sum of the flowrate Q1 of the first concentrated solution injected via the pump 19 into the main conduit 15 and the flowrate Q2 of the second concentrated solution injected via the pump 22 into the main conduit 15, while the concentration of potassium depends on the ratio of the flowrates Q1, Q2 of the first and second concentrated solutions. The concentration of sodium and of potassium in the dialysis liquid is chosen as a function of each individual patient. It can be set at a fixed value. According to the invention, for patients with hyperkalemia, the potassium concentration of the dialysis liquid is modified continuously during the treatment session according to a predetermined profile of variation.

EXAMPLE

Figure 2:
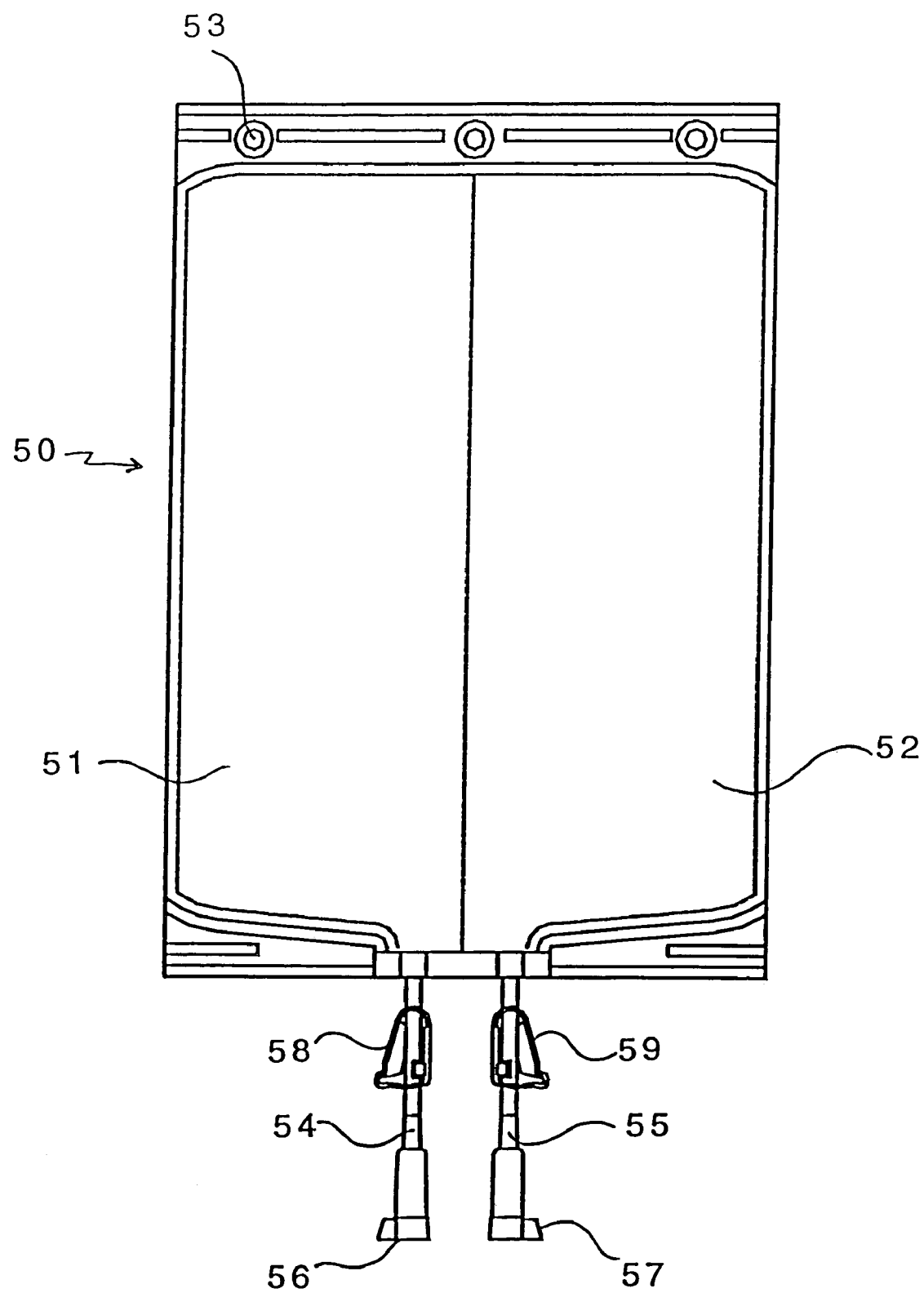
FIG. 2 shows a bag with two compartments for containing the two concentrated solutions from a treatment kit.

The hemodialysis system described above is equipped with a bag 50 made of flexible transparent plastic, as is represented in FIG. 2, and comprising two compartments 51 and 52 corresponding respectively to the containers 18 and 21 in FIG. 1. The bag 50 is provided in its upper part with eyelets 53 by which it can be suspended vertically from a suitable support. Each compartment 51, 52 is equipped at its base with an access tube 54, 55 provided at its end with a connection element 56, 57 intended to cooperate with a complementary connection element fixed to the end of the subsidiary conduits 16, 17 of the device 14 for preparation of dialysis liquid. A clip 58, 59 is arranged on each of the tubes 54, 55.

The compartment 51 (container 18) contains the following substances, in the following concentrations:

NaCl: 284.31 g/l
KCl: 19.57 g/l
CaCl2: 10.29 g/l
MgCl2: 2.63 g/l
Anhydrous glucose: 35 g/l.

The compartment 52 (container 21) contains the following substances, in the following concentrations:

NaCl: 284.31 g/l
KCl: 0 g/l
CaCl2: 10.29 g/l
MgCl2: 2.63 g/l
Anhydrous glucose: 35 g/l.

By means of these two solutions it is possible, according to the invention, to prepare a dialysis liquid having a sodium concentration of between approximately 130 mEq/l and approximately 155 mEq/l, and a potassium concentration varying, during a treatment session, from between an initial value of approximately 2.5 mEq/l and approximately 5.5 mEq/l and a final value of between approximately 1 mEq/l and approximately 2 mEq/l.

Figure 3:
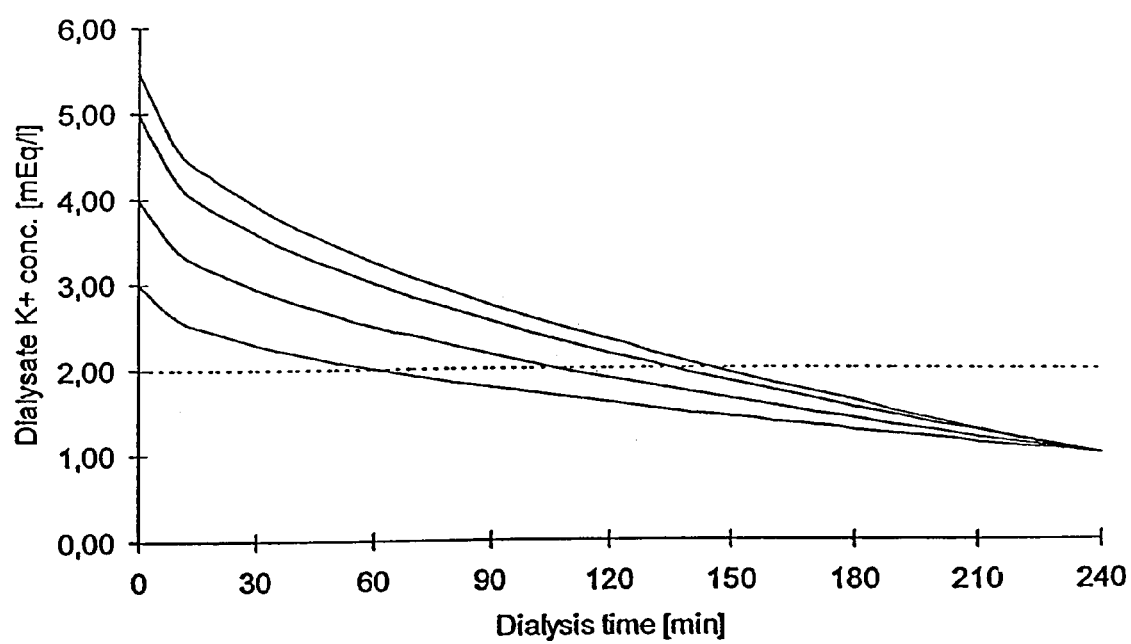
FIG. 3 is a graph showing several profiles of variation in the potassium concentration of a dialysis liquid.

FIG. 3 shows four profiles of variation of the potassium concentration of a dialysis liquid, which profiles can be obtained using the device 14 for preparation of dialysis liquid connected to the bag 50 with two compartments containing the concentrated solutions which have just been described. In this figure, the broken line shows the constant potassium concentration of a conventional dialysis liquid, that is to say 2 mEq/l.

The hemodialysis apparatus which has just been described functions in the following manner.

An operator inputs to the control unit 30, via the keyboard 32, conventional reference values corresponding to the various parameters of treatment (prescription), namely the blood flowrate Qb, the dialysis liquid flowrate Qd, the infusion flowrate Qinf of the bicarbonate solution, the total weight loss WL (quantity of plasma water to be withdrawn from patient by ultrafiltration), the total duration T of the session, and the sodium concentration of the dialysis liquid.

According to the invention, the operator also inputs, to the control unit, an information item or a series of information items concerning the potassium concentration of the dialysis liquid, which can be either a fixed reference value or one of the variation profiles stored beforehand in the control unit, corresponding for example to one of the graphs in FIG. 3. The operator can also create and store a profile appropriate to an individual client.

According to an alternative embodiment of the invention, the potassium concentration of the dialysis liquid is adjusted via the control unit 30 in the following manner: a dialysis-liquid having a potassium concentration corresponding to a predetermined reference value is initially circulated in the hemodialyzer 1, and this reference value is compared with the value of the potassium concentration in the spent liquid, measured by the probe 26. The control unit 30 subsequently controls the pumps 19, 22 of the device 14 for preparation of treatment liquid in such a way that the difference between the reference value and the measured value remains substantially equal to a given value, corresponding to a difference, acceptable for the patient, between the potassium concentration of the plasma and that of the dialysis liquid.

After a kit of concentrated solutions, such as the bag described above, has been connected to the conduits 16, 17 of the device 14 for preparation of dialysis liquid, the dialysis liquid circuit is filled with dialysis liquid. To do this, the main conduit 15 is connected to a source of running water and the pumps 19, 22, 25, 27 are started up. The pumps 19 and 22 are regulated via the control unit 30 in such a way that the potassium concentration and the sodium concentration of the dialysis liquid are equal to the corresponding reference values. The pumps 25, 27 for circulating dialysis liquid are regulated via the control unit 30 in such a way that the flowrate of the pump 25 situated upstream of the hemodialyzer 1 is equal to the reference flowrate Qd (500 ml/min, for example) and so that the flowrate of the pump 27 situated downstream of the hemodialyzer 1 is such that the flowrates measured by the flowmeters 24, 28 are equal.

At the same time as the dialysis liquid circuit is filling with the dialysis liquid according to the prescription, the circuit for extracorporeal blood circulation is rinsed and filled with sterile physiological liquid.

When priming of the dialysis liquid circuit and of the blood circuit is completed, the blood circuit is connected to the patient and the treatment proper can commence: the pumps 19, 22 of the device 14 for preparation of dialysis liquid, and the pumps 25, 27 for circulating the dialysis liquid, continue functioning, while the blood pump 6, the extraction pump 29 and the infusion pump 10 are started up. The blood pump 6 is set at the reference flowrate Qb (for example 200 ml/mn), the infusion pump 10 is set at the reference flowrate Qinf, and the extraction pump 29 is set at a flowrate QUF calculated by the control unit 30 on the basis of the reference values for total weight loss WL, infusion flowrate Qinf and total duration of treatment T.

The invention which has just been described is open to variants.

In the same way as the potassium concentration, the calcium or magnesium concentration can be adjusted to the needs of each individual patient.

With the preparation device according to the invention, it is possible to simultaneously adjust the potassium concentration of a dialysis liquid according to a first defined variation profile and the sodium concentration of the same dialysis liquid according to a second defined variation profile.

A probe for measuring the potassium concentration can be mounted on the supply conduit 12 in order to provide a measured value of the potassium concentration which will be used, for example, to calculate the difference between this value and the value measured downstream of the hemodialyzer 1 by the probe 26.

The invention claimed is:

1. A method for preparing a medical liquid from a liquid and two concentrated solutions, comprising the following steps:
    circulating the liquid in a preparation conduit;
    injecting into the preparation conduit, at a first injection flowrate Q1, a first concentrated solution containing at least sodium, potassium, and calcium and/or magnesium;
    injecting into the preparation conduit, at a second injection flowrate Q2, a second concentrated solution having, with respect to the first concentrated solution, the same concentration of sodium and of calcium and/or magnesium and a different concentration of potassium; and
    regulating the first injection flowrate Q1 and the second injection flowrate Q2 such that at any given time a diluted solution resulting from a mixing of the liquid and the first and second concentrated solutions has a desired concentration of sodium and of calcium and/or magnesium and a desired concentration of potassium.

2. A method according to claim 1, wherein the concentration of potassium in the second concentrated solution is equal to zero.

3. A method according to claim 1, further comprising varying over the course of time the first injection flowrate Q1 and the second injection flowrate Q2 of the concentrated solutions such that the concentration of potassium in the diluted solution varies over the course of time in accordance with a first concentration profile.

4. A method according to claim 3, wherein the first concentration profile is a descending profile whose initial value is between approximately 2.5 mEq/L and approximately 5.5 mEq/L and whose final value is between approximately mEq/L and whose final value is between approximately 1 mEq/L and approximately 2 mEq/L.

5. A method according to claim 1, further comprising varying over the course of time the first injection flowrate Q1 and the second injection flowrate Q2 of the concentrated solutions such that the concentration of sodium in the diluted solution varies over the course of time in accordance with a second concentration profile.

6. A method according to claim 5, wherein the second concentration profile is a constant profile according to which the concentration of sodium in the diluted solution remains substantially constant.

7. A method according to claim 6, wherein the liquid is circulated in the preparation conduit at a constant flowrate Q0, and a sum of the injection flowrates Q1 and Q2 of the concentrated solutions is maintained constant in such a way that the concentration of sodium in the diluted solution remains substantially constant.

8. A method according to claim 1, wherein bicarbonate is absent from the first and second concentrated solutions.

* * * * *

UNITED STATES PATENT AND TRADEMARK OFFICE
CERTIFICATE OF CORRECTION

PATENT NO. : 7,067,061 B2 Page 1 of 1
APPLICATION NO. : 10/844422
DATED : June 27, 2006
INVENTOR(S) : Antonio Bosetto and Francesco Paolini It is certified that error appears in the above-identified patent and that said Letters Patent is hereby corrected as shown below:

In claim 4, column 8, lines 20-21, delete "and whose final value is between approximately mEq/L".

Signed and Sealed this

Twelfth Day of September, 2006

JON W. DUDAS
*Director of the United States Patent and Trademark Office*